US009371182B2

(12) United States Patent
Hecht et al.

(10) Patent No.: US 9,371,182 B2
(45) Date of Patent: Jun. 21, 2016

(54) SPECIMEN ARCHIVE

(71) Applicant: GLP systems GmbH, Hamburg (DE)

(72) Inventors: Robert Hecht, Seehausen (DE); Andre von Froreich, Hamburg (DE)

(73) Assignee: GLP systems GmbH, Hamburg (DE)

( * ) Notice: Subject to any disclaimer, the term of this patent is extended or adjusted under 35 U.S.C. 154(b) by 462 days.

(21) Appl. No.: 13/849,727

(22) Filed: Mar. 25, 2013

(65) Prior Publication Data

US 2013/0287537 A1    Oct. 31, 2013

(30) Foreign Application Priority Data

Mar. 27, 2012  (EP) .................................. 12161434

(51) Int. Cl.
*B65G 1/04* (2006.01)
*G01N 35/04* (2006.01)
*B65G 1/127* (2006.01)

(52) U.S. Cl.
CPC ........... *B65G 1/04* (2013.01); *G01N 35/04* (2013.01); *B65G 1/127* (2013.01); *G01N 2035/042* (2013.01); *G01N 2035/0425* (2013.01); *G01N 2035/0427* (2013.01)

(58) Field of Classification Search
None
See application file for complete search history.

(56) References Cited

U.S. PATENT DOCUMENTS

| | | | |
|---|---|---|---|
| 5,921,739 A | 7/1999 | Keip | |
| 6,024,425 A * | 2/2000 | Imai | A47F 1/00 254/286 |
| 6,536,559 B1 * | 3/2003 | Siegler | B65G 1/127 187/223 |
| 7,214,023 B2 | 5/2007 | Sato et al. | |
| 2002/0102149 A1 | 8/2002 | Warhurst | |
| 2007/0172396 A1 * | 7/2007 | Neeper | G01N 35/00732 422/400 |
| 2008/0003083 A1 | 1/2008 | Solomon | |
| 2013/0129455 A1 * | 5/2013 | De Vries | B65G 1/0435 414/277 |
| 2014/0027242 A1 * | 1/2014 | Engle | A23L 3/04 198/347.2 |

FOREIGN PATENT DOCUMENTS

| | | | |
|---|---|---|---|
| DE | 102009041219 | 3/2011 | |
| EP | 1321386 | 6/2003 | |
| EP | 1321386 A2 | 6/2003 | |
| KR | WO 2009005222 A1 * | 1/2009 | ............ G01N 35/04 |
| WO | 2009077465 | 6/2009 | |

* cited by examiner

*Primary Examiner* — Jill Warden
*Assistant Examiner* — Benjamin Whatley
(74) *Attorney, Agent, or Firm* — Sand & Sebolt (57) ABSTRACT

An apparatus for archiving specimens in specimen vessels. The apparatus includes an archive room accessible via a lock for automated feeding of vessels into and out of the room. A storage and restacking system is disposed in the room and includes two side-by-side stacks of trays in a receiving area. Each tray has a receptacle area defining a plurality of receptacles therein, each configured to receive a single vessel. A stacking means forms the stacks of trays. One tray is stacked on another in such a way as to maintain a clearance relative to the receptacle area of the lower tray. A lifting means is provided for vertically lifting trays stacked on a selected tray; and a transfer means is provided for horizontal transfer of a selected tray from one stack to the other, or from one stack to the lock, or from the lock to one of the stacks.

8 Claims, 7 Drawing Sheets

SPECIMEN ARCHIVE

CROSS-REFERENCE TO RELATED APPLICATIONS

This application claims the benefit of European Patent Application Serial No. EP 12 161 434.1, filed Mar. 27, 2012.

BACKGROUND OF THE INVENTION

1. Technical Field

The invention relates to an apparatus for archiving a plurality of specimens contained in specimen vessels, particularly medical and/or biological specimens. The invention further relates to a method for removing a selected specimen vessel containing a specimen, particularly a medical and/or biological specimen, from an archive room.

2. Background Information

It is known in the art that, following completion of a specimen analysis, for example a medical specimen in a medical analysis laboratory, said specimen must be stored for a certain period of time, while clearly maintaining an identification and allocation of the specimen to a specimen origin, for purposes of documentation and conducting, for example, control analyses or further specimen testing. Correspondingly, in the context of ordering medical laboratory tests, it is not rare for physicians to initially order only limited testing of medical specimens, for example of blood samples, when giving the order to an analysis lab. Depending on the outcome of the initial analysis, the ordering physician may require further testing of the specimen to include additional analysis parameters. Analysis orders of this kind that are structured in two stages are intended to reduce the costs generated by the ordering physician, which are ultimately charged to the patient.

In medical analysis laboratories, but not only there, with increased frequency, there arise therefore situations when respective specimens must not only be archived but also removed again from the archive. In view of the enormously high throughputs in, for example, medical analysis labs and the need to automate a great proportion of the analysis work, not least of all due to the low compensation levels per analysis, there exists a demand for providing an archive system with a compact design that is still able to receive a plurality of specimens and allows, in addition, for the fast and targeted removal of individual specimens for follow-up processing.

The specimens therein, particularly medical and/or biological specimens, are typically stored in specimen vessels, which are often tubes or so-called vials.

Specimen archives like this used for archiving large numbers of such specimen vessels and specimens contained therein have, accordingly, tray-type sample carriers with an arrangement that accommodates a plurality of receptacles for receiving individual specimen vessels, particularly such tubes and/or vials. These tray-type sample carriers are then arranged inside the archive room, taking advantage of the spatial width and depth therein, as well as the height of the room.

An example of an archive and/or storage system of this type is disclosed in US 2007/0172396 A1. There, the inside of an archive room is accessible via a lock for infeeding and/or outfeeding specimens or specimen vessels loaded with specimens, respectively, to tray-type sample holders provided with specimen vessels. An elevator and/or carousel system with two continuously circulating vertical rows configured in the manner of a rotary elevator is contained in the archive room that includes a plurality of receptacle drawers suspended on a correspondingly continuously circulating drive train. Due to being disposed in an articulated manner on the drive system, the receptacle drawers are able to travel around turn-around points in a top and a bottom section of the "rotary elevator" such that the floor of the compartments always points downward. The corresponding specimens that must be stored are placed into these compartments. If a sample is to be deposited, the continuous drive is moved until such a time that a vacant compartment comes to be located across from the lock such that a specimen vessel and/or specimen holder with a plurality of specimen vessels can be placed therein after passing the lock. If a certain specimen is to be removed from the archive system, the compartment housing a specimen holder that contains the specimen is moved in front of the lock, by operating the drive system and the compartments suspended thereon, and the specimen holder is removed and extracted.

Disadvantageously, this system requires a large three-dimensional space for embodying the continuous drive system, particularly in the top and bottom sections of the archive room at the turn-around points; this volume is not available for specimen storage. In other words, the ratio of the number of possible specimens that can be stored and the necessary volume of the receptacle space is comparatively unfavorable, whereby the storage density of the specimens is correspondingly low. This means, in a limited space, it is only possible to store a small number or specimens, or a larger storage space must be provided for depositing a certain number of specimens, associated with additional expenditure. Particularly if a refrigerated storage of specimens is compulsory, as is required for various medical or biological specimens, such an unfavorable volume ratio also results in higher operating costs, as a comparatively small number of stored specimens requires the cooling of a comparatively large three-dimensional space.

In addition, outfeeding times are comparatively long for specimens if it is necessary to remove two specimens in sequence from a comparatively fully stocked archive that are located on different compartment levels. For example, if a comparatively large specimen sample carrier must be removed from a first storage space in a first compartment, the system is not able to advance the drive for moving the compartments already at that time and restack the compartments for the removal of a further, smaller sample carrier from another compartment, if only a smaller sample carrier must be removed from the further compartment. At any rate, after handling the first sample carrier from which a specimen is removed, said sample carrier cannot easily be returned into the archive; rather, it is necessary to move that compartment back to face the lock that offers a receiving space for the sample carrier. Especially, the dwelling time of specimens requiring refrigeration is thus prolonged inside the lock, which is typically not refrigerated, and can result in excessive heating of the further specimens located on the sample carrier, possibly damaging them.

A second embodiment of this specification discloses an alternative system that is particularly intended for storing specimens requiring deep-freezing. Provided inside a freezer-type archive room, there is a rack system of compartments or drawers rigidly arranged one top of each other, thus allowing only for a horizontal removal of a sample carrier. Toward one side, the archive room is closed off by vertically moveable insulating elements. On this side, outside of the actual archive room that is delimited by the insulating elements, there is provided an extraction manipulator that is movable in the vertical direction for targeting a position that is located higher or lower and upon which a sample carrier, which is to be extracted, is disposed. Said manipulator includes, furthermore, a lifting mechanism, which is brought to engage with the insulation elements via corresponding tabs, and is able to move this insulation element as well as any insulation elements resting thereupon in the vertical direction to create an opening inside the insulating wall composed of the insulating elements. A corresponding sample carrier is then removed from the rack system through this opening.

Although this solution allows for compact storage of the samples in the actual archive room, a large-dimensioned lock however, requires a corresponding amount of construction space in the vertical direction, because it is necessary to dispose a height-adjustable extraction system. Therefore, this solution also results in an unfavorable ratio of available space versus usage of space, accompanied by the associated excess costs.

A further archive system, operating in the manner of a rotary elevator, is disclosed in WO 2009/077465 A1. This system suffers from the same disadvantages as the system that was disclosed as the first embodiment in US 2007/0172396 A1.

A further possibility for archiving and storing specimens is disclosed in U.S. Pat. No. 7,214,023 B2. The specimen archive shown therein is constructed in the manner of a high-rise rack storage system based on known logistics applications. It has a plurality of rack storage areas, disposed adjacent relative to each other and vertically on top of each other, where the corresponding sample carriers, complete with specimen vessels, are placed. An extraction system is able to move between the rack storage areas both vertically as well as horizontally, whereby individual sample carriers are extracted from the storage.

The above system also suffers from the disadvantage that a space must be reserved for trips executed by the extraction system, which, once again, cannot be used as storage space in the archive room, resulting only in an unfavorable utilization of the archive room relative to the number of the specimens to be stored therein. This causes a particularly unfavorable cost effect when the archive room must be refrigerated.

SUMMARY

Based on this known prior art and the above-captioned archive systems, it is the object of the present invention to improve an apparatus for archiving a plurality of specimens contained in specimen vessels, particularly medical and/or biological specimens such that the same allows for particularly compact storage of the specimens in the archive room, while simultaneously providing more reliable, faster and easier accessibility of the stored specimens for extracting a selected specimen vessel. As a further aspect, the invention shall provide a method for extracting a selected specimen vessel containing a specimen, particularly a medical and/or biological specimen, from an archive room, allowing for simple and easy extraction from an archive room that is specified as compact.

First referring to the specification of the apparatus according to the invention, such an apparatus for archiving a plurality of specimens contained in specimen vessels, particularly medical and/or biological specimens, includes first of all, and in harmony with the prior art, an archive room that is accessible via a lock for automatic infeeding and outfeeding of specimen vessels. Disposed inside the archive room is a storage and redistribution system for specimen vessels that includes specimen trays with a plurality of receptacles for specimen vessels disposed on a receptacle area. The receptacles therein are configured such, in particular, that they can receive a single specimen vessel each, for example essentially cylinder-shaped receptacle openings for receiving tube-shaped specimen vessels, wherein the receptacles typically have holding devices disposed therein that hold the specimen vessels safely in place.

The apparatus according to the invention is characterized by the fact that the specimen trays include stacking means upon which there can be placed, for the purpose of constituting a stack of specimen trays, one further specimen tray respectively leaving a clearance relative to the receptacle area of the specimen tray located there-below. An upper specimen tray is therein deposited directly on the lower specimen tray without these trays being disposed one above the other by being suspended on a drive apparatus, however, leaving respective clearances between trays. The stacking means only ensure that the receptacle areas of the specimen trays, which are disposed one on top of the other, are arranged accordingly as to leave clearances relative to each other between trays. Such a clearance is necessary because, upon receiving the specimen vessels, said vessels rise in terms of their respective height to a level above the receptacle area, and the next loaded specimen tray must rest on a previous specimen tray loaded with specimen vessels, however, only on the stacking means but not on the specimen vessels.

To move the specimen tray inside the archive room and thereby extracting a selected specimen and/or specimen tray containing a corresponding specimen vessel in a targeted manner through the lock, and/or to be able to deposit a new specimen tray, a receiving space for at least two specimen stacks disposed adjacently relative to each other is further provided in the storage and restacking system; and two such specimen stacks, which are disposed adjacently relative to each other, are indeed present; and the storage and restacking system includes lifting means with vertical lift action of one or a plurality of a further selected specimen tray(s), which are stacked on a selected specimen tray; as well as transfer means for the horizontal transfer of a specimen tray from one stack to another stack, and/or from one of the stacks into the lock, and/or from the lock to one of the stacks. It is understood that more than one lock can be present, for example two locks arranged at two opposite sides in the archive room, through which specimen trays can be fed in and/or extracted.

Correspondingly, the apparatus according to the invention differs from the solutions as provided by the prior art (and relative to the solution operating in the manner of a rotary elevator according to US 2007/0172396 A1 and/or WO 2009/077465 A1) in that, in fact, no continuous drive mechanism is disposed therein that provides for and has disposed thereon receptacles for specimen trays and that would require a large construction space, particularly in the area of the upper and lower turnaround points of the continuous drive system. Instead, the solution according to the invention provides, rather, that the specimen trays are deposited directly on top of each other in stacks, with the stacks being disposed adjacently relative to each other, and thereby packed with maximum density. This also applies, in particular, for the bottom area close to the ground, as well as the opposite upper section of the archive room.

Comparatively minimal clearances suffice for moving the specimen tray out of one stack and either to another stack or through the lock to the exterior of the archive room, and by which the specimen trays that rest on the selected tray and, if need be, the selected specimen tray itself that is to be moved, must be lifted. The clearance that must be provided for this purpose, which must be disposed and/or provided in the upper area of the archive room for construction reasons, is sufficiently specified already by one complete height of a specimen tray (including the stacking means); it can be dimensioned even smaller. Due to the fact that the specimen trays themselves can be directly stacked on top of each other without the need for inserting further intermediate elements there between, in this instance as well, the available space is optimally utilized. In the known solution according to the prior art that called for a "rotary elevator," the individual specimen trays are disposed inside holders in such a way that there exists even greater play between the specimen trays such that space is being wasted in this regard as well.

In comparison to the alternative known solution involving stationary specimen trays in a receiving space, meaning, on the one hand, according to the second embodiment as disclosed in US 2007/0172396 A1 with an insulating wall of the archive room that is constructed of moveable elements, and a vertically movable removal device and/or according to a solution of a "high-rack storage" as disclosed in U.S. Pat. No. 7,214,023 B2, according to the inventive solution, there also exists the advantage of a visibly more compact construction because both devices, namely, on the one hand, a lock with a possible extraction means and, on the other hand, the archive room itself, can be configured in a more compact manner due to the fact that the specimen trays can be moved and restacked with a minimum space requirement for the clearance that must be adjusted between such specimen trays to be moved relative to each other. According to the invention, the corresponding adjustment of a space for manipulating a specimen tray from one stack to another stack and/or from a lock to a stack or vice versa is handled by the lifting means as provided by the invention, and the horizontal transfer is handled by the transfer means.

If refrigerated archiving of the specimen must be provided, the archive room can include a cooling means, and/or it can be connected to a corresponding cooling unit. It has been found that the apparatus according to the invention can be constructed with such compactness that a total of 21 specimen trays with a loading capacity of approximately 500sample vessels, particularly tubes, per specimen tray can be accommodated inside a conventional industrial and/or commercial refrigerator, for example, manufactured by the company Liebherr, having outside dimensions of a width of 1.4 m, a depth of 0.7 m and a height of 2 m, with inside dimensions of the cooling space of a width of approximately 1.2 m, a depth of 0.5 m and a height of 1.8 m. Correspondingly, inside a cabinet of this type, a storage capacity of approximately 10,500 specimens is obtained. Such a compact and dense storage capacity of specimens in such a restricted space has been unknown to date. Moreover, the fact that it is possible to rely on already existing commercial and/or industrial refrigerators, converting them for use as archive rooms, in that they must only be equipped accordingly with the storage and stacking systems including the lifting means, transfer means and the stacked specimen trays according to the invention, renders this solution an especially cost-effective alternative relative to implementing the invention and constructing such an apparatus for archiving specimens, which is visibly the most economical in comparison to the specialized solutions as required by the prior art.

Although many alternate solutions are conceivable as transfer means for moving a specimen tray from a first horizontal position, for example in a first stack, to a second horizontal position, for example in a second stack, for example as with conveyor belts, it is preferred according to an advantageous improvement of the invention for the transfer means to include at least one guideway, friction-reducing means disposed on the specimen tray, as well as means for moving a specimen tray, having friction-reducing means and resting on the guideway, along said guideway. In fact, a configuration of this kind calls for comparatively low maintenance and does not require any complex installation of extensive device units involving a great many small parts. Corresponding friction-reducing means on the specimen trays can be, for example, runners, sliding blocks, or the like. Preferred are, however, rolling means that are provided on the specimen trays, particularly wheels or rollers. The means for moving a specimen tray can be, for example, pneumatic or hydraulic cylinders having the corresponding engagement structures for the pneumatically or hydraulically actuated punch acting on a specimen tray and moving the same along the horizontal transfer direction. Also conceivable are, for example, gear drives having a gear that acts on a correspondingly toothed structure, for example a toothed rod, on the specimen tray, thereby moving the same in such a manner at least along one guideway in the horizontal direction. Said at least one guideway is configured therein accordingly so as to provide, in particular, low-friction engagement with the friction-reducing means on the specimen tray; this can be achieved, for example, by way of the interaction of runners or sliding blocks made of a low-friction plastic material such as, for example, Teflon, on the guideway. For the interaction with rollers or wheels, it is possible to envision such a guideway as a, for example, smooth metal or plastic surface, or the like.

If rolling means are provided on the specimen trays as a component of the transfer means, it is advantageous to dispose at least two guideways that are provided as a further component of the transfer means, and on which the rolling means run and/or roll when a horizontal transfer of a specimen tray from a first to a second position occurs. Said guideways therein can, according to a further advantageous embodied example of the invention, include moveable sections that are moved to complete the guideway, when the transfer means is activated, for the horizontal transfer of a specimen tray; otherwise they rest in a parking position in which the guideways are interrupted. Movable sections of this type in the context of the guideways are especially advantageous when the guideways themselves protrude into a vertical movement path of the specimen tray, particularly that of the rolling means, meaning they would be in the way during a lifting and/or lowering operation of the specimen tray and/or of a stack or partial stack of specimen trays. Using the solution that was described last, during a corresponding vertical movement of the specimen tray, it is possible for the moveable sections to rest in their respective parking positions, such that the rolling means are free to pass vertically. When a specimen tray, which must be moved via the guideways in the horizontal direction, has reached the position to which it was supposed to be moved via the guideway, the moveable sections for completing the guideways are moved out of the parking positions thereof in order to complete guideways. These corresponding moveable sections of the guideways can be pivoted, shifted or moved in any other way to achieve the above end; in particular, drive systems that can be automatically triggered such as, for example, pneumatic or hydraulic cylinders or motor-type drives, are provided for this purpose.

In a further advantageous embodied example of the invention, the stacking devices of the specimen trays include braces that are essentially vertical relative to the receptacle area and directed upward, and at each top end of the same there is disposed a pair of rollers. The axes of rotation of the respective pairs of rollers are parallel relative to each other and the rollers are disposed such as to leave a clearance there between. Respectively, the axes of rotation of the pairs of rollers are at the same distance therein relative to the receptacle area. Moreover, the specimen trays include rollers, which are disposed on a bottom side as well as positioned and dimensioned such that, when a specimen tray is placed on top of another specimen tray to constitute a stack, these rollers, which are disposed on the bottom side, come to lie on the pair of rollers disposed on the braces in such a way that at least one of the rollers, which are disposed on the bottom side of a top specimen tray, rests in the clearance between the pair of rollers on the brace of a lower specimen tray and is securely held therein to prevent any horizontal movement of the upper specimen tray. The roller, which is disposed on the bottom side of the specimen tray, is held therein by the lateral surfaces of the rollers that are disposed on the braces.

This construction achieves two purposes:

On the one hand, this configuration allows for safe and aligned stacking of the specimen trays in the vertical direction, and thereby the formation of at least two stacks in a correspondingly dense and compact stacking mode. On the other and, the rollers allow for vertical movement of the individual specimen trays via the transfer means after the specimen tray that is to be transferred has been detached from the adjacent specimen trays thereof via the lifting means and has been released relative to the same. As provided particularly for a transfer in the lower area, meaning on the floor of the archive room and/or receiving space, it is possible therein to utilize the rollers that are disposed on the bottom side of the specimen tray, or also, however, the rollers that are disposed on the ends of the braces, which then run hung-up on the corresponding guideways, as on a cableway. On specimen trays having a rectangular or square shape, in particular, one roller each is disposed on the bottom side in the area of each of the four corners, particularly on the longitudinal sides, and one pair of rollers each is disposed on the end of a brace disposed at that location; meaning a total of four rollers is disposed on the bottom side of a specimen tray and eight rollers, namely four pairs of rollers, are disposed on the top ends of the braces.

In the apparatus according to the invention, it is preferred for lifting and transfer means to be disposed in the storage and restacking system, respectively in the top and bottom areas of the receiving space such that specimen trays can be lifted off the two stacks, respectively one top specimen tray from the further specimen trays in the respective stack, and transferred to the respective other stack, particularly to the top position thereon; and it is preferred that for both stacks, respectively, the further specimen trays and/or the entire stack resting respectively on a bottom-most specimen tray is lifted, and a bottom-most specimen tray can be transferred from one stack to another stack, particularly into the bottom-most position thereof. This way, it is possible to implement the possibility of a rotating restacking operation of the specimen trays in two adjacent stacks, wherein a corresponding circulation can occur in both directions, meaning clockwise and counter-clockwise. As a matter of principle, it is also possible herein to provide not only two, but also a third or even further stacks, wherein the handover points for the transfer of a specimen tray must be provided between the stacks in positions 1 and 2, as well as between the stacks in positions 2 and 3 in order to be able to convey the corresponding specimen trays in all instances to a lock, which is provided only, for example, adjacent to stack no. 1. In an arrangement of this kind, it can make senses to provide a second lock on a side that is opposite the side of the archive room with the first lock, such that it is possible to extract specimen trays from stacks in positions 1 and 3, and feed specimen trays into these stacks.

Using the lifting and transfer means, it is possible to very quickly restack, for example, two stacks of specimen trays that are stacked adjacently relative to each other and move the same in such a way that a certain specimen tray, which houses, for example, a certain, specimen that must be extracted from the archive, and the related tray is conveyed in the direction of the lock, from which it can be finally extracted via the transfer means. Advantageously, the implementation and embodiment according to the invention allows that, while the extracted specimen tray undergoes further processing, for example the specimens and/or the specimen vessel that is/are to be extracted are removed from the specimen tray, a further extraction order is already being prepared inside the archive room, for example for extracting a further specimen vessel that is disposed on a different specimen tray, to the point that the stacks with the specimen trays are restacked once again as described above, until a specimen tray that must be extracted subsequently is located in the area of the lock. Due to the fact that, in particular, the initially extracted specimen tray does not have to be returned and resorted at exactly the same position from which it was taken, rather that it can be moved to any other location between two specimen trays, the same can be fed in wherever it is possible to extract the further specimen tray, already located in the area of the lock, very quickly, and the next specimen can be removed without delay.

If the lock is disposed in the area of the upper or lower end, respectively, of the receiving space, it is possible, as described previously, for the lifting and transfer means disposed at that location to be used not only for the handover between stacks, but also for feeding in and extracting specimen trays. However, for individual applications, it makes practical sense or has proved beneficial for a lock to be disposed in the middle area relative to the vertical height of a stack of specimen trays. In that case, it is envisioned that, in the area of the stack of the specimen trays, which is directed toward the lock, lifting and transfer means are disposed in a, seen in vertical direction, middle section such that the lifting means is able to lift a further specimen tray and/or a plurality of such further specimen trays, located above a specimen tray in an extraction position above the lock, and that further, a specimen tray located in the extraction position can be lifted and detached from the specimen tray located there below. Moreover, the arrangement occurs such that the transfer means is able to subsequently extract the thus released specimen tray through the lock. Vice versa, the lifting and transfer means are disposed in the section referred to such that for the feeding-in operation, a partial stack is lifted off the stack of specimen trays using the lifting means, and a clearance is created in the extraction position; and it is possible to move a specimen tray through the lock and into said free space via the transfer means.

Lifting means can basically be configured such that a lifted specimen tray or a corresponding stack of trays and/or a partial stack of trays is held continuously. For example, lifting means of this kind are able to grasp, by means of fork-type manipulation elements, under an edge of a specimen tray; for example powered by hydraulic or pneumatic cylinders or, however, by motor-type power, thus lifting the manipulation means, and thereby the corresponding specimen trays. In the alternative, the use of other lifting means is conceivable as well.

Due to the fact that particularly the number of the lifting means is to be limited to a minimum, while they simultaneously have to lift, in several consecutive steps, different partial stacks of specimen trays, total stacks or even individual specimen trays, it can be advantageous for the apparatus to include parking elements that can be activated and deactivated for temporarily parking a (partial) stack of specimen trays and/or an individual specimen tray lifted by the lifting means, which taken by itself can be understood to represent a partial stack comprising only a single unit. Parking elements of this kind, for example, can be pivoted from a structure that surrounds the receiving space into the area of the receiving space, or they can be bars or locks that can be moved in another manner allowing a state, after having been moved into the receiving space, in which they are activated for depositing the specimen tray on such elements.

For purposes of organization and operation of the apparatus according to the invention, the same should include a controller having a memory for storing the respective position of a specimen vessel on the associated specimen tray, as well as the position of the associated specimen tray in the stacks of specimen trays. Naturally, for purposes of reversible archiving of a specimen and/or a specimen vessel, it is crucial that the position of the same is known. To this end, the position of a specimen vessel, in which the same has been deposited on the specimen tray, is recorded and stored in a controller. Similarly, the specimen tray itself and/or the position thereof is stored in the controller. This can be achieved, for example, in such a way that the controller stores the transfer movements of the specimen tray between the stacks and the lifting movements, such that any wanderings of a specimen tray in the context of a circular passage through the stacks of trays are saved, as are any feeding-in and/or extraction operations of such a given tray; finally, based on these data alone, the controller "remembers" the respective position of the specimen tray. In the alternative or in addition, it is possible to mark the specimen trays with identification labels, for example RFID tags or barcodes, or the like, that interact with corresponding reader means within the apparatus, particularly in the receiving space in order to determine the identity of the respective specimen tray. This way, it is possible to reconstruct as to whether a specimen tray, as it is routed by the reader means, is in fact the tray that accommodates the sought after specimen. It makes particular sense to dispose a reader means in a position in the area before the lock, where the specimen trays are fed into the apparatus and extracted from it. This way, it is possible to double-check the identity of a specimen tray one more time before the extraction operation; and after a tray has been fed into the apparatus, it is possible to ascertain the identity thereof and proceed with recording and storing the now (newly) assigned position of the tray in the context of the stack of trays.

The invention, furthermore, discloses a method for extracting a selected specimen vessel containing a specimen, particularly a medical and/or biological specimen, from an archive room that includes an extraction opening. Said archive room, which can and/or is to be configured particularly as described previously, stores a plurality of specimen vessels on a plurality of specimen trays that are stored in two stacks disposed adjacent relative to each other, with the trays immediately one on top of the other that can be individually removed from the stacks. The method according to the invention is characterized by the fact that specimen trays are alternately transferred from the top position of a first stack to the top position of a second stack, and subsequently from a bottom position of the second stack to a bottom position in the first stack. Thus, in a first step, first a top specimen tray is lifted from the first of the two stacks and transferred to the second stack, then deposited in the upper-most position of that stack on top of the specimen tray that was previously in the very top position thereon. Then a partial stack of further specimen trays resting on a specimen tray that is disposed in the bottom-most position of the second stack is lifted from this specimen tray disposed at the very bottom, and the entire first stack is lifted. Subsequently, the specimen tray that is disposed in the bottom-most position of the second stack is transferred to the bottom-most position in the first specimen stack, and the previously lifted first stack is placed on the now transferred specimen tray.

This restacking of specimen trays is continued until a target specimen tray, on which the selected specimen vessel is located, is in a position adjacent to the extraction opening. Any partial stack of further specimen trays resting thereon, possibly still located on the target specimen tray, is then lifted from the target specimen tray, the target specimen tray is lifted, if necessary, off any partial stack disposed beneath said target specimen tray, then the target specimen tray is extracted from the archive room via the extraction opening. The selected specimen is then removed from the target specimen tray.

BRIEF DESCRIPTION OF SEVERAL VIEWS OF THE DRAWINGS

Further characterizing features and advantages of the invention can be derived from the subsequent description of an embodiment based on the enclosed figures. Shown therein are as follows.

The figures depict a possible embodiment of the apparatus according to the invention for archiving a plurality specimens contained in specimen vessels, hereafter referred to in short as the "archive apparatus," with illustrations of individual components and parts relevant according to the invention. The figures are drawn in a schematic fashion and certainly not true to scale. Also, not all structural details are shown. The representation is limited to the components that are essential for a possible implementation of the embodiment.

DETAILED DESCRIPTION

Figure 1:
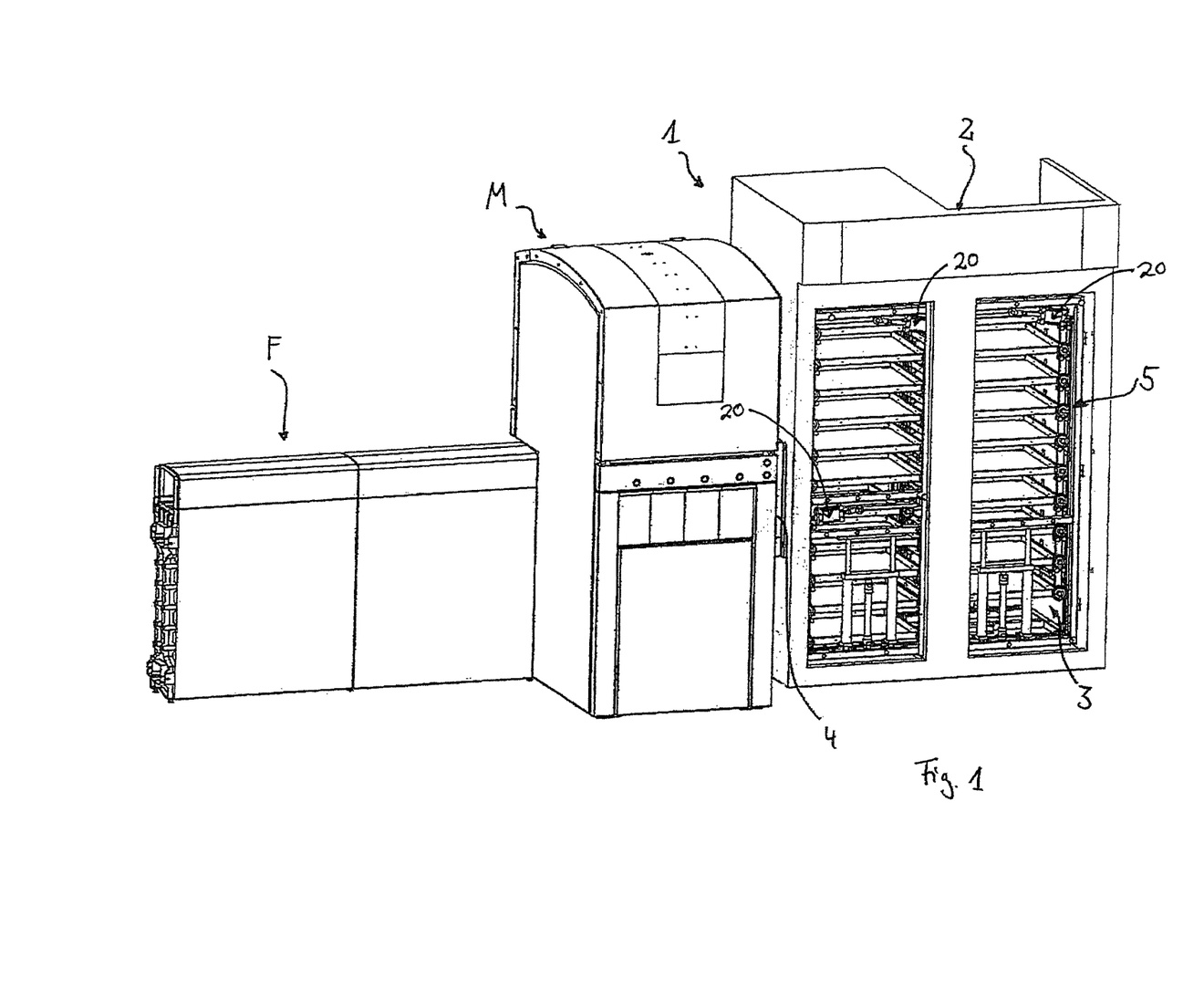
FIG. 1 shows a three-dimensional view of an archive apparatus according to the invention with connection to an automated conveying system for specimen vessels.

FIG. 1 shows an embodiment of an archive apparatus according to the invention, referred to as 1, that is connected to a train of an automatic conveying system F, presently only depicted in sections, for conveying, in particular, individual specimen vessels. The archive apparatus 1 comprises an archive cabinet 2 containing an archive room 3 therein. The archive cabinet 2 in the present embodiment is equipped with a refrigeration unit (not shown in further detail) for cooling the inside space, meaning the archive room 3. The present archive cabinet 2 is a commonly available commercial or industrial refrigerator having a double door, as sold by the company Liebherr, which has integrated therein an additional opening for a lock 4. Lock 4 is laterally connected to the archive cabinet 2, which can only be seen schematically in the representation and by which the archive room 3 is accessible from the outside. A manipulator unit M is connected to lock 4; the manipulator unit is not a component of the actual archive apparatus 1 in the narrow sense. Individual specimen vessels can be captured by a corresponding robotic arm inside the manipulator unit M, placed on transport vehicles or removed from the same and sorted into specimen receptacles having a plurality of receptacle openings, particularly specimen trays.

Figure 2:
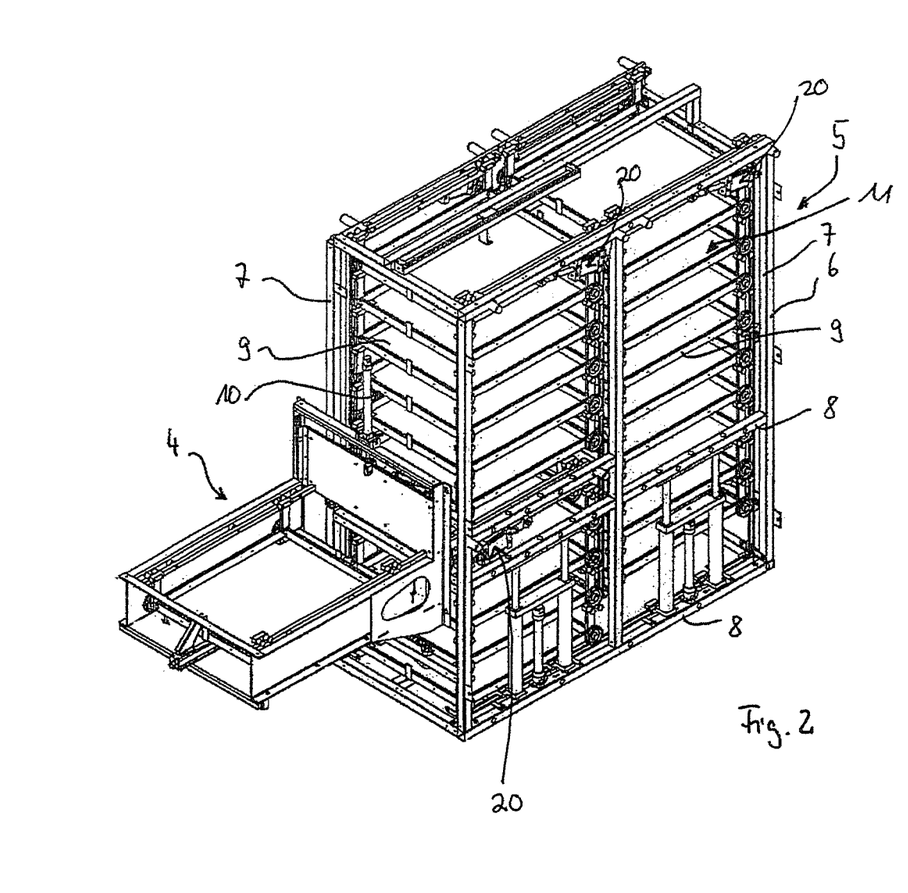
FIG. 2 shows a perspective view of the use of a storage and restacking system of the archive apparatus according to FIG. 1 with allocated lock.

A storage and restacking system 5 is disposed on the inside of the archive room 3. This system is depicted in the next FIGS. 2 and 3 separately from the archive cabinet 2 and will be explained below based on these representations. The storage and restacking system 5 first includes a framework structure 6 with vertical bars 7 and horizontal bars 8. A receiving space for specimen trays 9 is created inside the framework structure 6. Said specimen trays are stacked in the receiving space immediately on top of each other to constitute two stacks 10, 11 that are adjacent relative to each other. Stack 10 therein is the stack in which the specimen trays 9 make contact by the front sides thereof, as shown in the figures on the left side, with the front wall of the framework structure 6, disposed on which there is lock 4. Stack 11 is located on the side that is directed away from lock 4.

Figures 4, 4A:
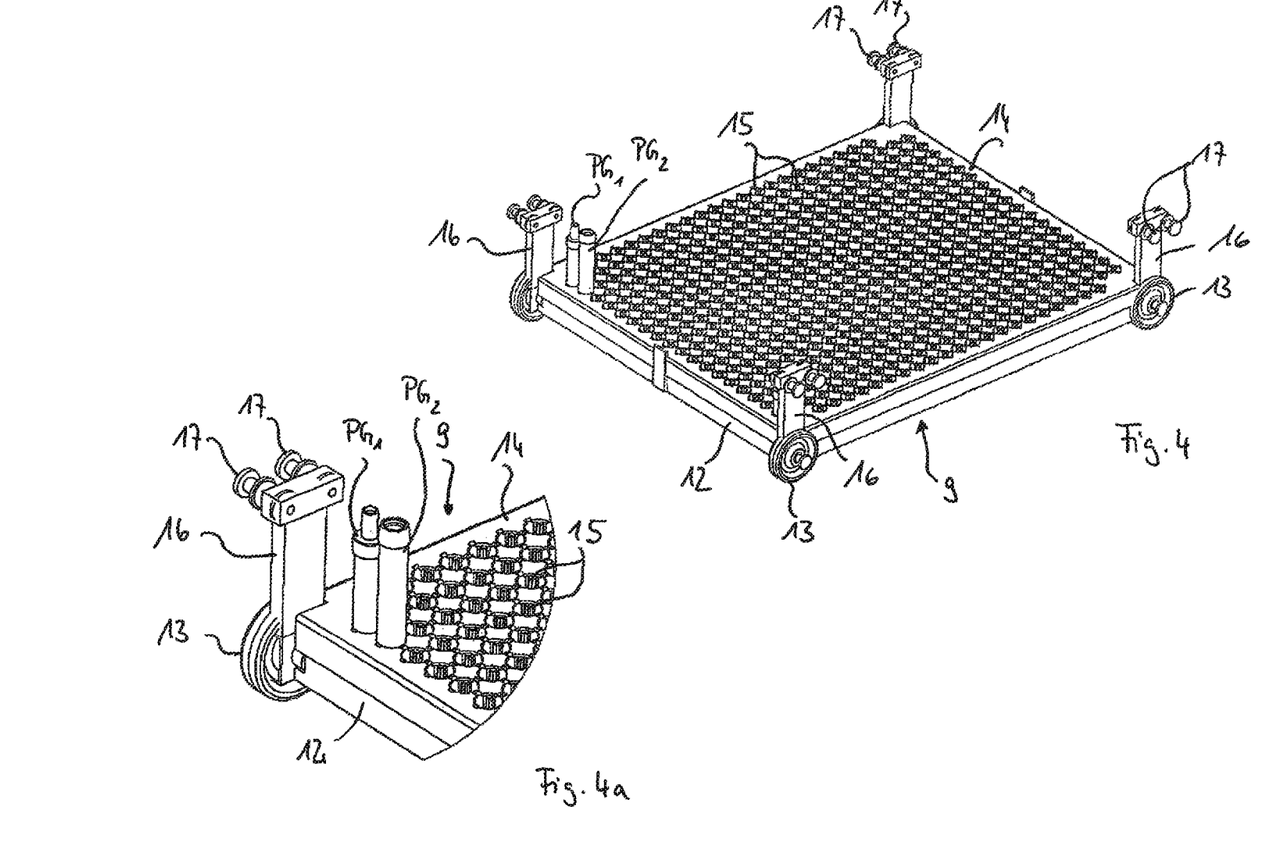
FIG. 4 shows a specimen tray of the archive apparatus according to the invention.
FIG. 4*a* shows an enlarged detail from the specimen tray according to FIG. 4.

The specimen trays 9 will be described first in further detail based on FIGS. 4 and 4a; the specimen tray as illustrated in FIG. 4 is shown in further detail by way of an enlarged detail in FIG. 4a. All specimen trays 9, which are basically components of the storage and restacking system 5, are configured, overall, in the same way, particularly identically, in the context of the present system. They have a basic frame 12 that encloses a rectangular inside area, and having rollers and/or wheels 13, which are disposed in the four corner positions, protruding from an underside thereof, respectively. A receptacle area 14 is placed on top of the basic frame 12, complete with lines and rows of densely packed receptacle openings 15 ready to receive a single tube-shaped specimen vessel each. To illustrate, two specimen vessels $PG_1$ and $PG_2$ are depicted as disposed in two receptacle openings 15 of the receptacle area 14. It can be seen very nicely therein that the specimen vessels $PG_1$ and $PG_2$ visibly protrude from the surface of the receptacle area 14, meaning the side of the receptacle area 14 located above the rollers and/or wheels 13.

Also visible in the area of the four corners of the rectangular area of the basic frame 12 and/or the receptacle area 14 are braces 16, protruding upward. At the upper end of each brace 16, there is disposed a pair of rollers 17 having axes of rotation that are parallel relative to each other and parallel relative to the receptacle area 14, disposed each at the same distance relative to the same. The positions of the rollers 17 therein provides that the clearance between the rollers 17 is such that, with aligned and stacked specimen trays 9, one roller and/or one wheel 13, respectively, of the second specimen tray 9 deposited on top of the first specimen tray 9 fits into this clearance and is received therein such that it is securely held in place and horizontally immovable. This type of stacking operation can be seen very nicely especially in FIG. 3. The braces 16 and the rollers 17 and 13 therein are dimensioned such that the receptacle area 14 of a specimen tray 9 located in stack 10 or 11, respectively, maintains a sufficient clearance relative to a further specimen tray 9 by the underside thereof relative to the top side of the receptacle area 14 of the specimen tray 9 disposed below the former, such that the specimen vessels disposed in receptacle openings 15, for example $PG_1$ and $PG_2$, do not make contact with the bottom side of the receptacle area 14 of the upper specimen tray 9. Instead there exists a sufficient amount of play or a sufficient clearance, respectively.

Figure 3:
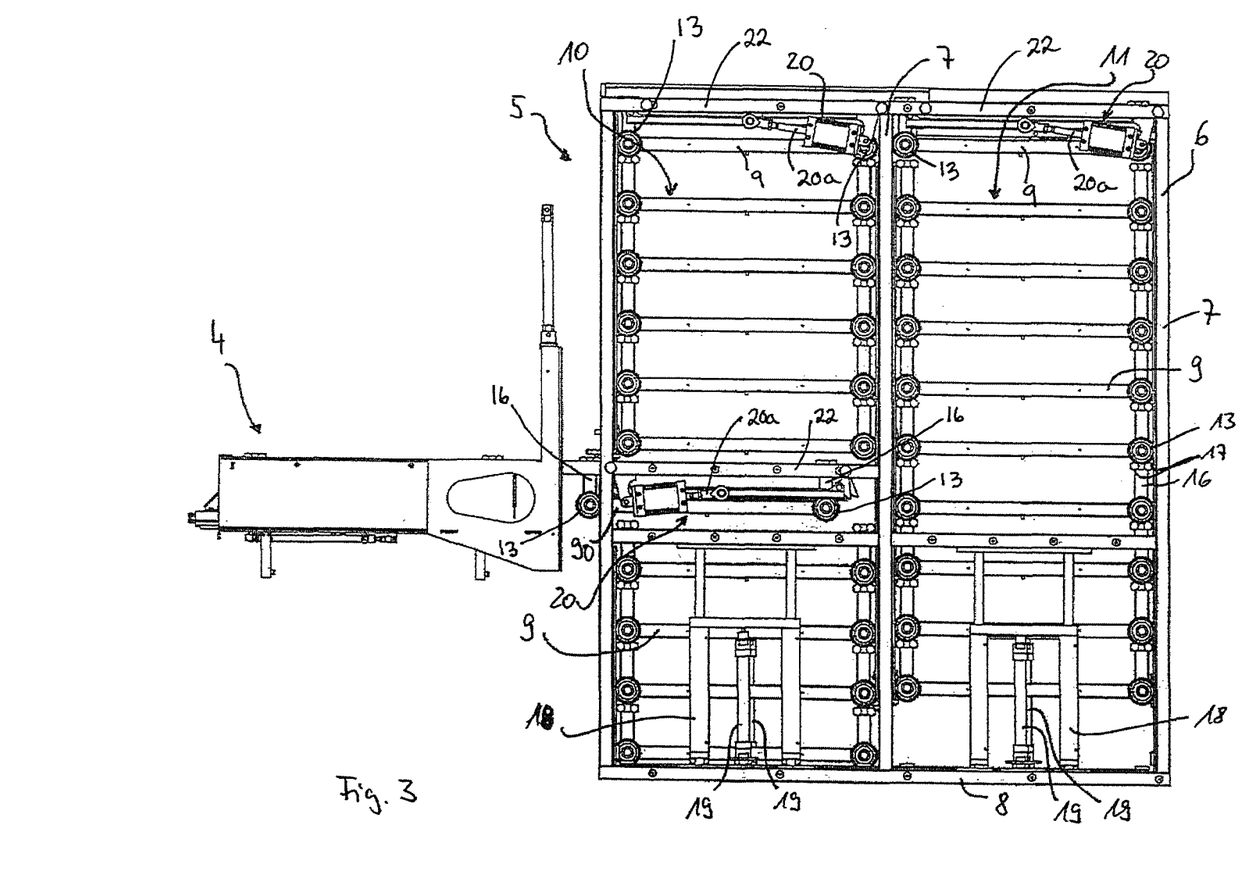
FIG. 3 shows a representation of the storage and restacking system with allocated lock according to FIG. 2, seen in a side view.

Referring once again to FIGS. 2 and 3, two lifting means 18 can be detected in the storage and stacking system 5 depicted therein; one is disposed laterally in the area of stack 10, one laterally in the area of stack 11. Each of the shown lifting means 18 is composed of a pair of lift devices 19 that are disposed opposite each other along the narrow side of the specimen trays 9, as disposed in stacks 10 and/or 11. Using the lift devices 19, it is possible to lift the stack of specimen trays 9 in a vertical direction. Furthermore, transfer means 20 are depicted in the area opposite the lock 4 as well as at the upper end, wherein transfer means are also present in the bottom area of the framework structure 6, not shown in further detail. Using the transfer means, it is possible to transfer individual specimen trays 9 in a horizontal direction from one position to another, particularly from stack 10 to another stack 11 and/or in the reverse direction, or from stack 10 in the direction of the lock 4. This is indicated in FIG. 3, for example, when a position is depicted in which a specimen tray 90 is just then moved in the direction of the lock 4. The modalities of this movement and the prerequisites that must be in place for it to occur will be described in further detail below.

Figure 5:
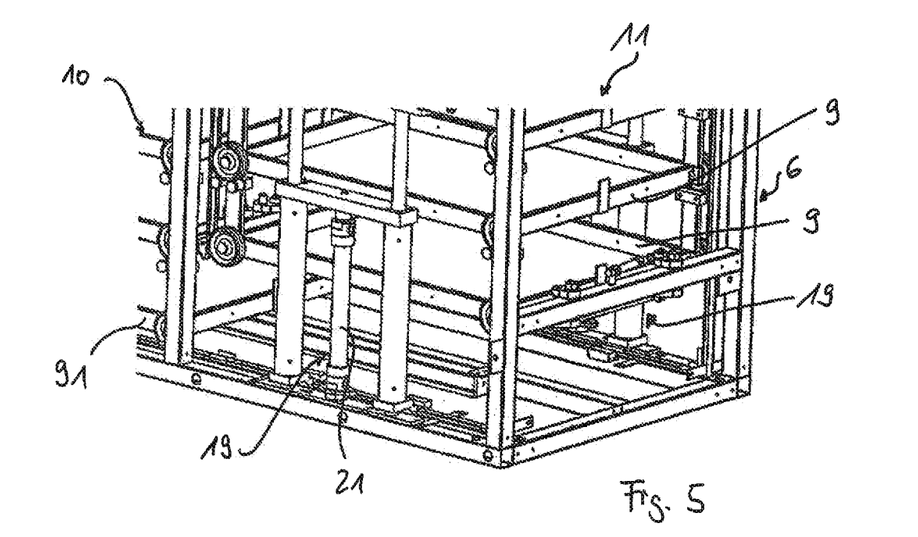
FIG. 5 shows a detail of the storage and restacking system for a representation of the lifting means.

FIG. 5 depicts once more an enlarged detail of the bottom area of the framework structure 6 with the lifting means 18 envisioned at that location and composed of two lift devices 19. For example, the lift devices 19 have a hydraulically actuated lift cylinder 21, by which it is possible for a manipulation element, not shown in further detail, to be able to engage with a specimen tray 9, and be able to lift the same, if necessary with further specimen trays 9 that are deposited and stacked thereon. Correspondingly, FIG. 5 shows stack 11, of which only a partial detail is presently seen, in a position in which the same is lifted completely, This means the bottom-most specimen tray 9 of stack 11 no longer rests on the base of the framework structure 6, but rather, it has been moved vertically upward. In this position, it is now possible for a bottom-most specimen tray 91 from stack 10, shown only suggestively, from which the next upper specimen tray has been lifted (which has not occurred yet in the representation in the drawing), to be transferred from stack 10 to the bottom-most position of stack 11, in that it is moved by a transfer means, presently not shown in further detail, for example a pressure cylinder, rolling along on rollers 13 until it reaches the bottom-most position of stack 11. Stack 11 can then be lowered again by the lift devices 19 such that the previously bottom-most specimen tray of stack 11 is now placed and securely stacked by the wheels 13 thereof on the presently completely transferred specimen tray 91, more specifically on the rollers 17 or the clearances there-between at the top ends of braces 16, respectively, of specimen tray 91.

In stack 10, the specimen tray that was previously second to the bottom but has now become the bottom-most specimen tray is lowered and deposited on the base of the framework structure 6 and/or on the bottom-most position of the receiving space that is delimited by this framework structure 6.

Figure 8:
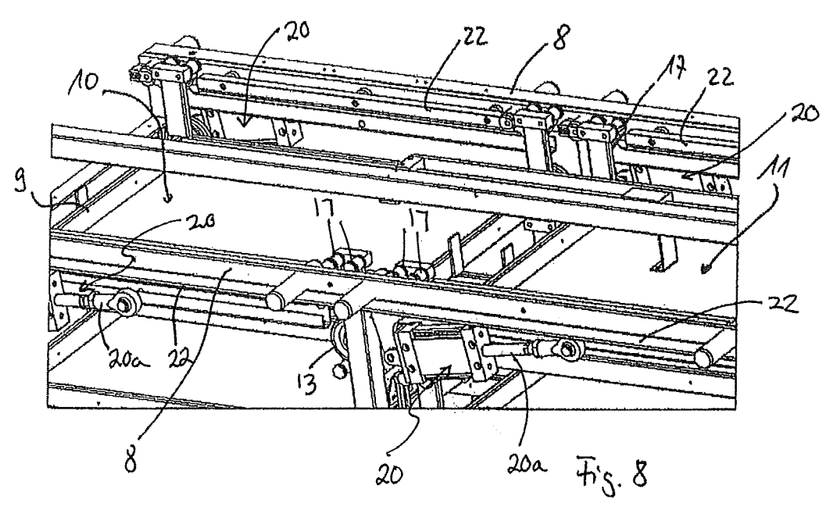
FIG. 8 shows, in a representation of a detail, the storage and restacking system to illustrate the guideways located therein.

The top-most position is handled similarly, as shown in FIG. 8. Rails 22 can be seen here on the horizontal bars 8 of the framework structure 6 whereupon rollers 17 of the top-most specimen tray 9 are able to run. The means for moving a specimen tray 9 can be, for example, pneumatic or hydraulic cylinders 20a (FIGS. 3 and 8) having the corresponding engagement structures for the pneumatically or hydraulically actuated punch acting on a specimen tray 9 and moving the same along the horizontal transfer direction. Also conceivable are, for example, gear drives having a gear that acts on a correspondingly toothed structure, for example a toothed rod, on the specimen tray 9, thereby moving the same in such a manner at least along one guideway (i.e., rail 22) in the horizontal direction. Said at least one guideway 22 is configured therein accordingly so as to provide, in particular, low-friction engagement with the friction-reducing means (such as rollers or runners 13, 17) on the specimen tray 9; this can be achieved, for example, by way of the interaction of runners or sliding blocks made of a low-friction plastic material such as, for example, Teflon, on the guideway 22. For the interaction with rollers or wheels 13, 17, it is possible to envision such a guideway 22 as a, for example, smooth metal or plastic surface, or the like. The rails 22 are interrupted in the area where the rollers 17 run, wherein these interruptions can be filled in by moveable rail sections (presently not shown in further detail), and the rails 22 can thus be completed. If the top position in a stack is vacant, particularly if stack 10 is not occupied by a specimen tray 9 (in the figure, the top-most shown specimen tray 9 is not present), then, if detached from the specimen trays 9 there below, which means the further stack 11 has been lowered by a measure, a top-most specimen tray 9 can be transferred by moving the same along the rails 22, which have been closed by the movement of the moveable elements, into the top-most position on stack 10. If a transfer of this kind occurs after, as described previously based on FIG. 5, a transfer of specimen tray 91 from stack 10 to stack 11 has occurred, and if these processes are repeating and recurrent, there occurs a piece-by-piece restacking of the specimen trays 9 in stacks 10, 11 in a counterclockwise circulation, seen from the perspective of FIG. 3. In a reverse movement direction, the circulation can be adjusted to a clockwise direction.

Figure 6:
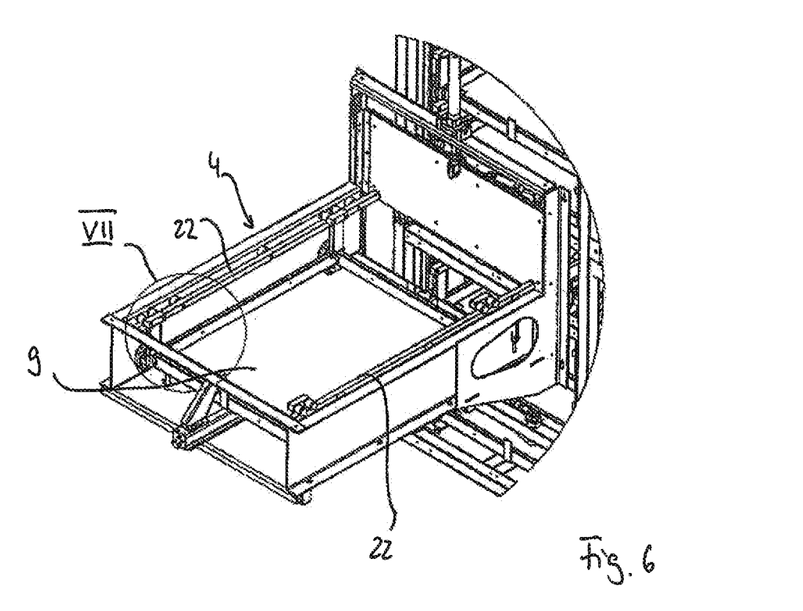
FIG. 6 shows, in a representation of a detail, the lock with a specimen tray located therein.
Figure 7:
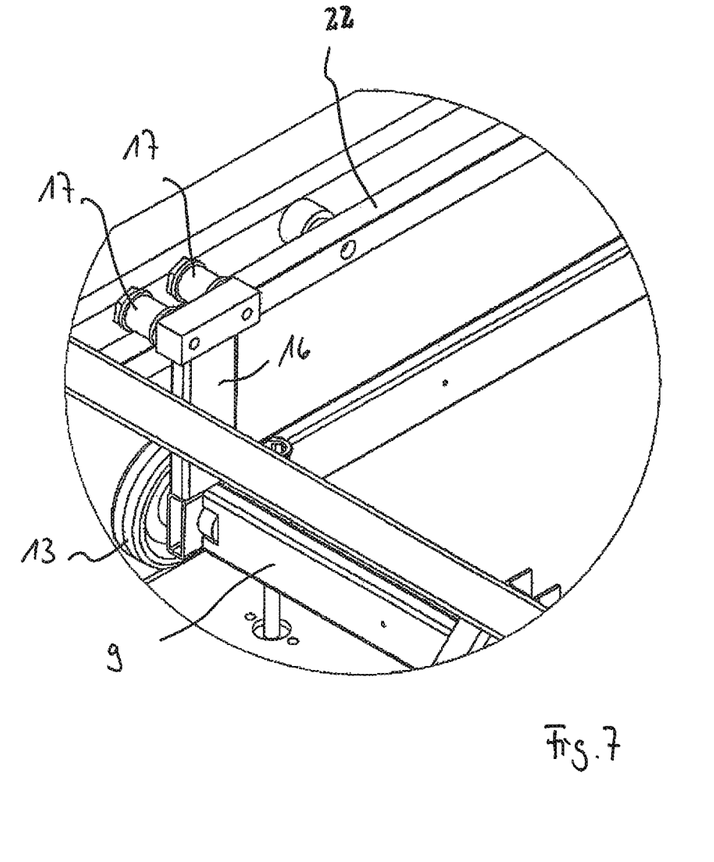
FIG. 7 shows, in a still further enlarged representation, the detail that is marked by a circle VII in FIG. 6.

FIGS. 6 and 7 show how the transfer of a specimen tray into the lock 4 is handled. In fact, rails 22 are disposed at that location as well, along which rollers 17 at the top ends of the braces 16 are able to roll. To be able to extract such a specimen tray 90 (see FIG. 3) from stack 10 and transfer the same into lock 4, any further specimen trays 9 resting on this specimen tray 90 are lifted by means of the lifting means 18 allocated to this stack 10. Furthermore, specimen tray 90 itself is lifted a bit, and the rails 22, which are also disposed in the middle area, flush relative to lock 4, are completed by incorporating the moveable sections, such that the specimen tray 90 can be moved by the transfer means disposed therein out of stack 10 and into lock 4.

The moveable sections of rails 22 are located therein in positions in which there are disposed, in stacks 10 and/or 11, the wheels and/or rollers 13 and the rollers 17, as well as braces 16. In a normal parking position, they release the section in the rails 22 where the rollers and/or wheels 13, 17 move in a vertical direction, such that they are able to pass on the rails 22. Only when the movable sections are moved from a parking position into a position in which they complete the rails 22, do the rollers 17 grasp behind the rails 22 and are held thereon. This way, it is possible for a specimen tray 9, which has been brought with the rollers 17 thereof in a position above a rail 22, and for which the moveable section of rails 22 is closed, to be held in this position, even when the lifting means 18 once again lower the respectively lifted stack 10 or 11. Correspondingly, not only the rails 22 are closed for a transfer occurring in the horizontal direction; simultaneously, the specimen tray that is to be moved is separated from the remainder of the specimen trays 9 inside the stack, such that is can be moved out of stack 10 or 11 altogether, to be moved either to the other of the stacks 11 or 10, respectively, or the lock 4.

Figure 9:
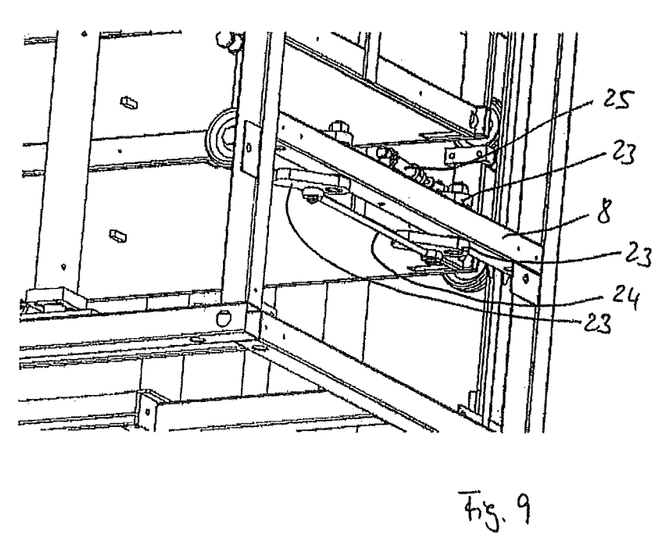
FIG. 9 shows a further detail of the storage and restacking system with depicted parking elements.

A further possibility for maintaining specimen trays 9 at an elevated height is provided as well. As can be seen in FIG. 9, pivotable locking pieces 23 are disposed on some of the front-side horizontal bars 8 that are coupled via a linkage 24. By means of a cylinder 25 that can be activated pneumatically or hydraulically, it is possible to pivot the locking pieces 23 from their resting positions, in which they are located substantially parallel relative to the horizontal bar 8, into a transverse position relative to the former. The locking pieces 23 therein are pivoted into the movement space of the specimen trays 9 by their free ends, thus constituting a deposit area on the bottom side, wherein further locking pieces 23 lock the specimen tray 9 on the top side. If a stack, for example stack 11, has been placed in total or, however, by way of a partial stack on the locking pieces 23, the lifting means 18 is able to lift a further partial stack. In the alternative, any placement of the stack on the locking pieces 23 can also serve to relieve the load that the lifting means 18 are subjected to.

The above description should have made it clear that an essential advantage and core feature of the present invention is to be found in the fact that the storage and restacking system 5 of the archive cabinet 2 places individual specimen trays 9 immediately on top of each other, wherein, with the aid of the lifting and transfer means, specimen trays 9 can be moved in front of the lock, removed and extracted, and/or a specimen tray 9 can be fed-in into any position in stack 10, meaning presently between any pair of previously stacked specimen trays 9. To move a desired specimen tray to an area across from the lock 4, the specimen trays 9 are restacked in succession in the manner as described above by transferring, respectively, individual specimen trays into the bottom-most and/or top-most positions from one stack to another stack until the desired specimen tray is located across from lock 4 by lifting partial stacks and separating the same from a specimen tray disposed there-below, and until the same can be transferred into the lock 4 using the transfer means.

In this embodiment, the archive system 1 also includes a controller, which is not shown in further detail, that includes, in particular, a memory means for storing the positions of individual specimen trays, as well as the positions of individual specimen vessels on the specimen trays. Correspondingly, using these data, the controller can initiate an automated restacking operation of the specimen trays in archive room 3 until the specimen tray carrying the sought after specimen has reached the position across from the lock and be can extracted from there. By way of a supporting measure, the archive apparatus 1 can further be provided with a specimen tray recognition system to which end each specimen tray must bear a unique identification and archive room 3 must allow for the possibility of disposing a corresponding reader device for reading the identification markers.

LIST OF REFERENCE SIGNS

1 Archive apparatus
2 Archive cabinet
3 Archive room
4 Lock
5 Storage and restacking system
6 Framework structure
7 Vertical bar
8 Horizontal bar
9 Specimen tray
10 Stack 11 Stack
12 Basic frame
13 Roller or wheel, respectively
14 Receptacle area
15 Receptacle
16 Brace
17 Roller
18 Lifting means
19 Lift device
20 Transfer means
21 Lift cylinder
22 Rail
23 Locking piece
24 Linkage
25 Cylinder
90 Specimen tray
91 Specimen tray
F Conveyor system
M Manipulation unit
$PG_1$ Specimen vessel
$PG_2$ Specimen vessel

The invention claimed is:

1. An apparatus for archiving a plurality of specimens contained in specimen vessels particularly medical and/or biological specimens, said apparatus comprising:
an archive room that is accessible via a lock for automated feeding-in and extraction of specimen vessels into and out of the archive room;
a storage and restacking system for the specimen vessels disposed in the archive room, said system including a plurality of specimen trays, each specimen tray having a plurality of receptacles disposed on a receptacle area for receiving specimen vessels;
stacking devices configured to engage the specimen trays; wherein the stacking devices are braces pointing upward from each of the trays, essentially vertically relative to the receptacle area, wherein in order to form a stack of specimen trays, a first one of the plurality of specimen trays is engaged with one or more braces extending vertically upward from the trays, thereby becoming a lower specimen tray in the stack, and a further specimen tray is positioned vertically above the lower specimen tray, thereby becoming an upper specimen tray in the stack; and the upper specimen tray is engaged with the one or more braces while maintaining a clearance relative to the receptacle area of the lower specimen tray;
wherein a receiving space is provided in the storage and restacking system and at least a first stack and a second stack of specimen trays are disposed adjacent each other within the receiving space; wherein the lock is located laterally adjacent the first stack; and wherein the storage and restacking system further comprises:
a lifting means for vertically lifting or lowering one or more of the plurality of specimen tray(s); and
a transfer means for horizontal transfer of any selected specimen tray from the first stack to the second stack; or from the second stack to the first stack; or from the first stack to the lock or from the lock to the first stack; and wherein the transfer means includes:
at least one guideway provided in the receiving space;
a friction-reducing means disposed on each of the plurality of specimen trays; wherein the friction-reducing means are rolling means including a pair of first rollers provided proximate an upper end of each brace; said pair of first rollers having parallel axes of rotation and maintaining a clearance there-between, said first rollers being disposed aligned respectively at an equal distance relative to the receptacle area; and second rollers disposed proximate a bottom side of each of the plurality of specimen trays positioned and dimensioned such that these second rollers, upon placement of the upper specimen tray onto the lower specimen tray, come to rest on the first rollers disposed on the braces in order to a form the respective one of the first and second stacks; and wherein one of the second rollers of the upper specimen tray rests in the clearance between the rollers of a first roller pair on a respective one of the braces of the lower specimen tray and is securely held therein to prevent any horizontal movement of the upper specimen tray; and
a means for moving a selected specimen tray resting on the at least one guideway by the friction-reducing member along the at least one guideway.

2. The apparatus according to claim 1, wherein the lifting and transfer means are disposed in the receiving space of the storage and restacking system such that, from the first and second stacks of specimen trays a specimen tray in a top-most position in either of the first and second stacks is liftable by the lifting means from a remaining group of specimen trays in the respective stack and is transferrable by the transfer means to the other stack, particularly into the top-most position thereon, and such that the specimen trays in the first or second stack that rest on a bottom-most specimen tray and/or the entire first or second stack is liftable by the lifting means and the bottom-most specimen tray from the respective stack is transferrable by the transfer means to the other stack, particularly into a bottom-most position thereof.

3. The apparatus according to claim 1, wherein, one of the specimen trays is located in a middle section of the first stack of specimen trays and is positioned laterally adjacent the lock in an output position and wherein the lifting and transfer means are disposed such that, using the lifting means, the specimen trays located above the one of the specimen trays laterally adjacent the lock are lifted, and the one of the specimen trays adjacent the lock is lifted and detached from the specimen tray located there below, and subsequently the one of the specimen trays is extracted via the transfer means through the lock and/or, by lifting a partial stack of specimen trays via the lifting means, a free space is created in the output position, and the one specimen tray is movable via the transfer means through the lock into this free space.

4. The apparatus according to claim 1, further comprising locking pieces that are activatable and deactivatable for the temporary parking of a partial stack of specimen trays that was lifted by the lifting means.

5. The apparatus according to claim 1, wherein the apparatus includes refrigeration for cooling the archive room.

6. The apparatus according to claim 1, further comprising a controller connected to a memory for storing the respective position of a selected specimen vessel on an associated specimen tray as well as the position of the associated specimen tray in the first or second stacks of specimen trays.

7. The apparatus according to claim 1, further comprising an identification label provided on each of the plurality of specimen trays and at least one reader means for detecting the identification labels in the receiving space.

8. The apparatus as defined in claim 1, wherein the rolling means on the bottom side of the plurality of specimen trays are wheels instead of second rollers.

* * * * *